(12) United States Patent
Völcker et al.

(10) Patent No.: US 6,473,239 B2
(45) Date of Patent: Oct. 29, 2002

(54) IMAGING SYSTEM WITH A CYLINDRICAL LENS ARRAY

(75) Inventors: Martin Völcker, Königsbronn (DE); Christof Fattinger, Basel (CH)

(73) Assignee: Carl-Zeiss-Stiftung (DE)

( * ) Notice: Subject to any disclaimer, the term of this patent is extended or adjusted under 35 U.S.C. 154(b) by 0 days.

(21) Appl. No.: 09/835,172

(22) Filed: Apr. 12, 2001

(65) Prior Publication Data

US 2002/0030894 A1 Mar. 14, 2002

Related U.S. Application Data

(63) Continuation of application No. PCT/EP99/06925, filed on Sep. 18, 1999.

(51) Int. Cl.[7] .................. G02B 27/10; G02B 27/12; G02B 3/06; G02B 9/00; G01J 1/58
(52) U.S. Cl. .................. 359/624; 359/640; 359/710; 250/486.1; 356/127
(58) Field of Search ............... 250/206.1, 216, 250/486.1, 576; 356/123, 127, 141, 621, 622, 623, 624, 639, 640; 359/710

(56) References Cited

U.S. PATENT DOCUMENTS

| | | | | |
|---|---|---|---|---|
| 4,642,526 A | * | 2/1987 | Hopkins | 315/244 |
| 5,150,259 A | * | 9/1992 | Oishi | 359/619 |
| 5,574,790 A | * | 11/1996 | Liang et al. | 380/23 |
| 5,602,679 A |   | 2/1997 | Dolgoff et al. | 359/640 |
| 5,808,784 A |   | 9/1998 | Ando et al. | 359/443 |
| 5,861,256 A | * | 1/1999 | Glass et al. | 435/6 |
| 6,177,667 B1 | * | 1/2001 | Fujita et al. | 250/216 |

FOREIGN PATENT DOCUMENTS

| | | | |
|---|---|---|---|
| DE | 197 48 211 A1 | 10/1997 | G02B/23/12 |
| EP | 0 631 434 A1 | 6/1994 | H04N/5/74 |
| JP | 07013101 | 1/1995 | G02B/27/18 |
| JP | 09113858 | 5/1997 | G02F/1/13 |
| WO | WO 97/34171 | 9/1997 | |

* cited by examiner

Primary Examiner—Georgia Epps
Assistant Examiner—David N. Spector

(57) ABSTRACT

The invention relates to an imaging system for optical automatic analysers, especially fluorescence readers. On the sample side, the imaging system contains a cylindrical lens array and a prism array, which is arranged upstream of the cylindrical lens array. The prismatic effect of the prisms of the prism array lies in the direction of the cylinder axes of the cylindrical lenses. Together with a telescopic imaging system, the inventive imaging system creates a number of parallel cylindrical focussing volumes between the cylindrical lens array and a detector array, these focussing volumes being slanted towards the optical axis of the telescopic system in relation to the vertical. The arrangement enables the detection of fluorescence with a large aperture in one direction, and at the same time enables depth selective analysis of the fluorescence signal, especially the discrimination of the fluorescent radiation originating from the solution above.

10 Claims, 4 Drawing Sheets

FIG. 4a        FIG. 4b
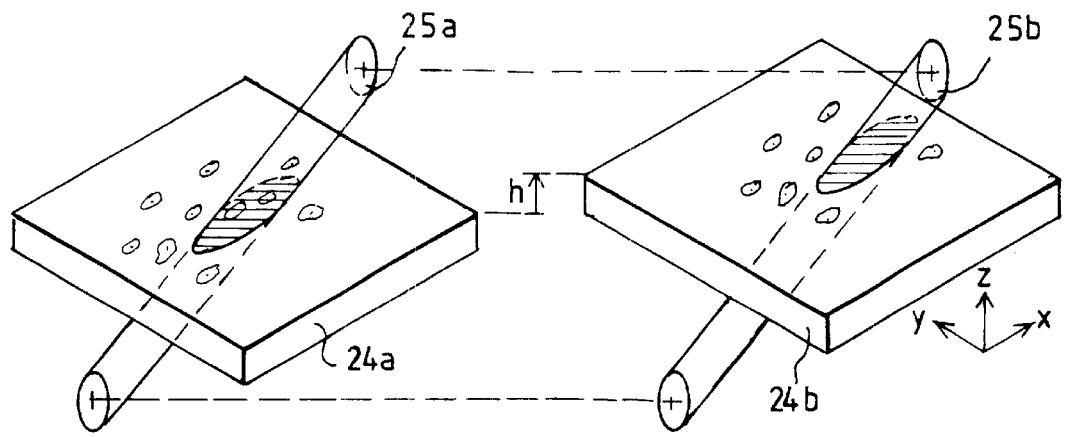
FIG 5a        FIG. 5b
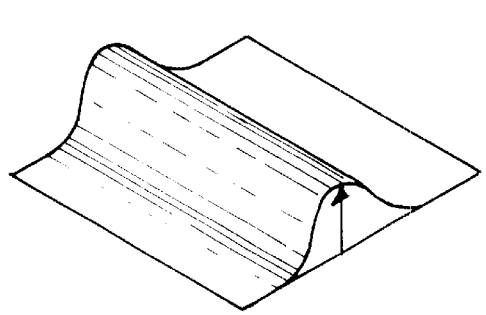
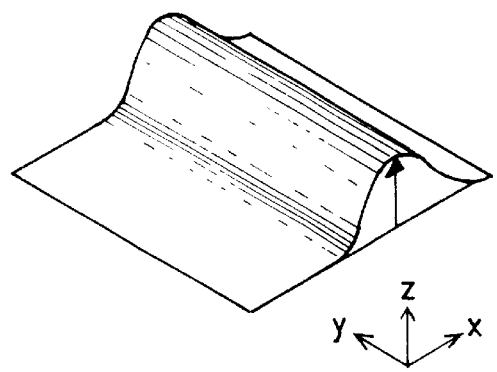
FIG. 6a
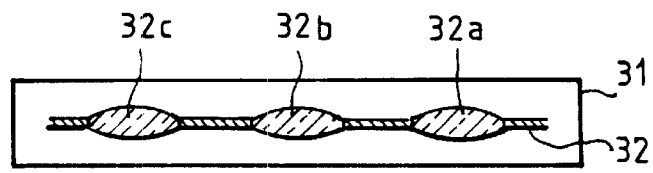
FIG. 6b
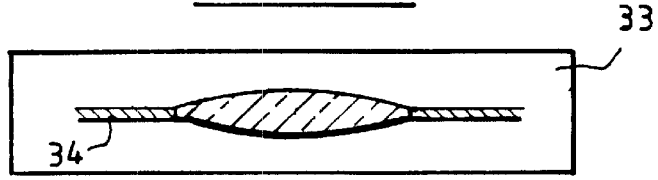

IMAGING SYSTEM WITH A CYLINDRICAL LENS ARRAY

This application is a continuation of PCT/EP 99/06925, filed Sep. 18, 1999.

The invention relates to an imaging system, in particular for automatic analyzers with a high sample throughput. Such automatic analyzers are frequently termed "readers" or "fluorescence readers" for microtiter plates. Such "readers" are used, for example, in the development of pharmaceutically active materials or in molecular medical diagnoses, and thus in applications in which fluorescence, luminescence, and absorption investigations of large sample numbers and very small sample quantities are required. Consequently a high sample throughput is of great importance in these applications. On the other hand, measurements of reaction kinetics are frequently required, the time constants of which are an obstacle to a high sample throughput.

In these applications, microtiter plates are used, with very small sample containers arranged in an array, in standardized embodiments with, e.g., 96 or a multiple thereof, for example, 384 or 1536, sample containers. As an alternative, so-called substance chips are also in use as sample containers.

In a few applications, the actual task of the measurement is to determine the fraction, or the change with time of the fraction, of a substance which has penetrated from the solution into the interior of a cell or which is bound to the cell surface. The substance concerned is as a rule marked with a fluorescing dye. In this measurement task, it is required to discriminate the fluorescence signal of the dye taken up by, or bound to, the cell from the fluorescence signal of the substance still present in the solution. Since the cells concerned are as a rule situated on the floor of the microtiter plate, a fluorescence reader is consequently required which operates floor-selectively.

A corresponding floor-selective fluorescence reader is offered, for example, by the Molecular Devices Corporation, USA under the name Fluorometric Imaging Plate Reader. In this device, the fluorescence excitation takes place from below through the floor of the microtiter plate at a strongly grazing incidence through a slit mask. The fluorescence light is then detected from that lateral region of the microtiter plate into which the excitation light has penetrated to only a small depth into the sample container, due to the grazing incidence. However, the fluorescence excitation is very ineffective with this device, since only a small fraction of the excited fluorescence is used for the detection. Furthermore, only the fluorescence of a very small lateral region of the sample space floor is used, so that only the cells situated in this small lateral region contribute to the measurement signal.

A line-form imaging system is known form JP 7013101-A in which an array of pentaprisms is arranged between two lens arrays. The lens arrays respectively have a cylindrical lens surface on the side toward the pentaprisms. The pentaprisms then bring about a lateral interchange of the image effected by the whole system in the direction of the axes of the cylindrical lenses.

In the Applicant's as yet unpublished German patent application 197 48 211, an optical system for a corresponding analytical device is described, in which a lens array with a lens allocated to each sample container is provided on the sample space side. Together with a telescope with a field lens, arranged after the lens array on the detection side, the foci of the individual lenses of the lens array are imaged on a detector array for the production of the desired measurement signal. Signal acquisition here takes place in parallel and simultaneously for all the sample containers, so that a high throughput can be realized with this optical arrangement. Since the measurement signal, for example the detected fluorescence light, originates almost exclusively from the focal volumes of the individual lenses of the lens array, a very depth-selective fluorescence detection is possible with this optical arrangement. Here also, the lateral cross section, that is, perpendicular to the optical axes of the lenses of the lens array, of the detection volume is of course very small. Furthermore, the detection of the fluorescence or of another measurement signal from the region of the floor of the sample container requires in practice a depth scan, and thus several measurements with different distances between the microtiter plate and the optical arrangement in the direction of the optical axis, since the individual floors of the sample containers of the microtiter plate have different heights, due to production conditions. The time required for a depth scan is however contrary to the aim of a high sample throughput.

The present invention has as its object to provide an imaging system which makes possible measurements in parallel in plural sample containers. The measurement signals acquired in parallel are to have an identical sensitivity in all the sample containers, even when the floor height of the sample containers is different, and to make possible a discrimination of the measurement signals originating from the region near the floor, and a high sample throughput.

This object is attained according to the invention by an imaging system with the features of claim 1. Advantageous developments of the invention will become apparent from the features of the dependent claims.

The imaging system according to the invention consequently has an array of cylindrical lenses. A prism array is arranged before this cylindrical lens array on the sample side, the prism array being oriented relative to the cylindrical lens array such that the prismatic effect of the prisms is in the direction of the cylinder axes of the cylindrical lenses. The cylindrical lens array and the prism array can be constituted here as two separate components or as a single component. In the latter case, the combined array has, on a common support, a constitution as a prism array on the sample side and the cylindrical lenses on the side remote from the sample. Due to the cylindrical lenses, a substantially cylindrical detection volume results in each of the sample containers. Due to the prisms arranged on the sample side in front of the cylindrical lenses, the cylinder axes of the focal volume receive an inclination relative to the cylinder axes of the cylindrical lenses. If the cylindrical lens array is arranged substantially parallel to the microtiter plate, cylindrical detection volumes thereby result which are inclined to the floors of the sample containers. Since the cross sectional surfaces through the detection volumes are identical for parallel sections through these detection volumes, the detection of the measurement signal from different depths of the sample volume takes place with identical sensitivity. Consequently even different floor heights in the different sample containers do not give rise to different measurement sensitivities.

It should be mentioned at this point that an imaging system for the projection of color LCD displays as the object to be imaged is already known from U.S. Pat. No. 5,602,679, in which a lens array with a superposed prismatic effect is used. Cylindrical lenses are also stated there as a possible lens form of the lens array. Although no specific data are given, it is to be concluded therefrom that the prism action of the prisms has to be oriented perpendicular to the cylinder axes of the cylindrical lenses, so that the desired superposition of the color pixels is attained. Apart from this, the statement of objects given there completely departs from the statement of object of the present invention.

The imaging system according to the invention is preferably used, similarly to that of the German Patent Application 197 48 211 mentioned hereinabove, together with a telescopic imaging system, the long-focus lens of the telescopic imaging system being oriented in the direction toward the cylindrical lens array, and overlapping with its diameter plural, preferably all the, cylindrical lenses. A detector array is then preferably arranged after the imaging system or the telescopic imaging system, and with it the measurement light for the different parallel channels of the imaging system is detected in parallel. The detector array is then furthermore preferably arranged behind the exit-side focal plane of the telescope lens remote from the cylindrical lens array, the said focal plane being remote from the long-focus telescope lens and the cylindrical lens array. With such an optical arrangement, different lateral displacements of the intensity distribution of the measurement light on the detector array result from different heights of the floor of the microtiter plate. Since as a rule the maximum measurement signal, for example, the maximum fluorescence intensity, originates from the transition region from the sample space floor into the solution, the measurement signal resulting from this region can thereby be easily discriminated from the remaining measurement signal in that only the regions of the detector array with maximum signal strengths are made use of for further evaluation. In this manner, the measurement signal originating from the floor region can quickly and easily be discriminated from the measurement originating from the solution.

The imaging system according to the invention can in principle be combined with the telescopic imaging system and the detector array into a single constructional unit. However, a modular construction is particularly advantageous, in which the cylindrical lens array and the prism array form their own constructional unit. This constructional unit can then be easily exchanged for the lens array from the above cited patent application 197 48 211, so that the functionality of the reader described there can be correspondingly enlarged. Alternatively, a reader constructed according to the present invention can easily be changed to a reader according to DE 197 48 211 by exchange of the constructional unit with the lens array on the sample side, and by insertion or exchange of a spacing ring for a constructional unit with a field lens between the two telescope lenses.

In the present invention, the apertures of the cylindrical lenses are imaged on the detector array by the telescopic imaging system.

For the excitation of fluorescence or luminescence, a vertical illuminator is to be provided, light from which is reflected into the measurement beam path, preferably between the detector array and the short-focus telescope lens.

In a completely automatic analyzer with an optical imaging system according to the invention, an evaluation computer for the evaluation of the light signals detected with the detector array is to be provided. This evaluation computer can carry out an integration of the light signals belonging to each sample container, in the direction perpendicular to the cylinder axes of the cylindrical lens array, and then, by means of software, determine solely the maximum value of the integrated light intensity or the other characteristic signal change in the direction of the cylinder axes of the cylindrical lenses, in order to thereby discriminate the measurement signal originating from the floor region of the sample volumes.

Details of the invention are described in more detail hereinbelow with reference to the embodiment examples shown in the Figures.

FIGS. 4a and 4b show graphical illustrations of two cylindrical focus volumes relative to two sample space floors with different floor heights;

FIGS. 5a and 5b show graphical illustrations of the intensity distributions on the detector array with the different floor heights according to FIGS. 4a and 4b;

FIG. 6a shows a module with a lens array with rotationally symmetrical lenses, which module can be exchanged for the imaging system according to the invention, in a modular type of construction, and FIG. 6b shows, in a modular type of construction, a module with a field lens which can be inserted between the telescope lenses.

Figure 1:
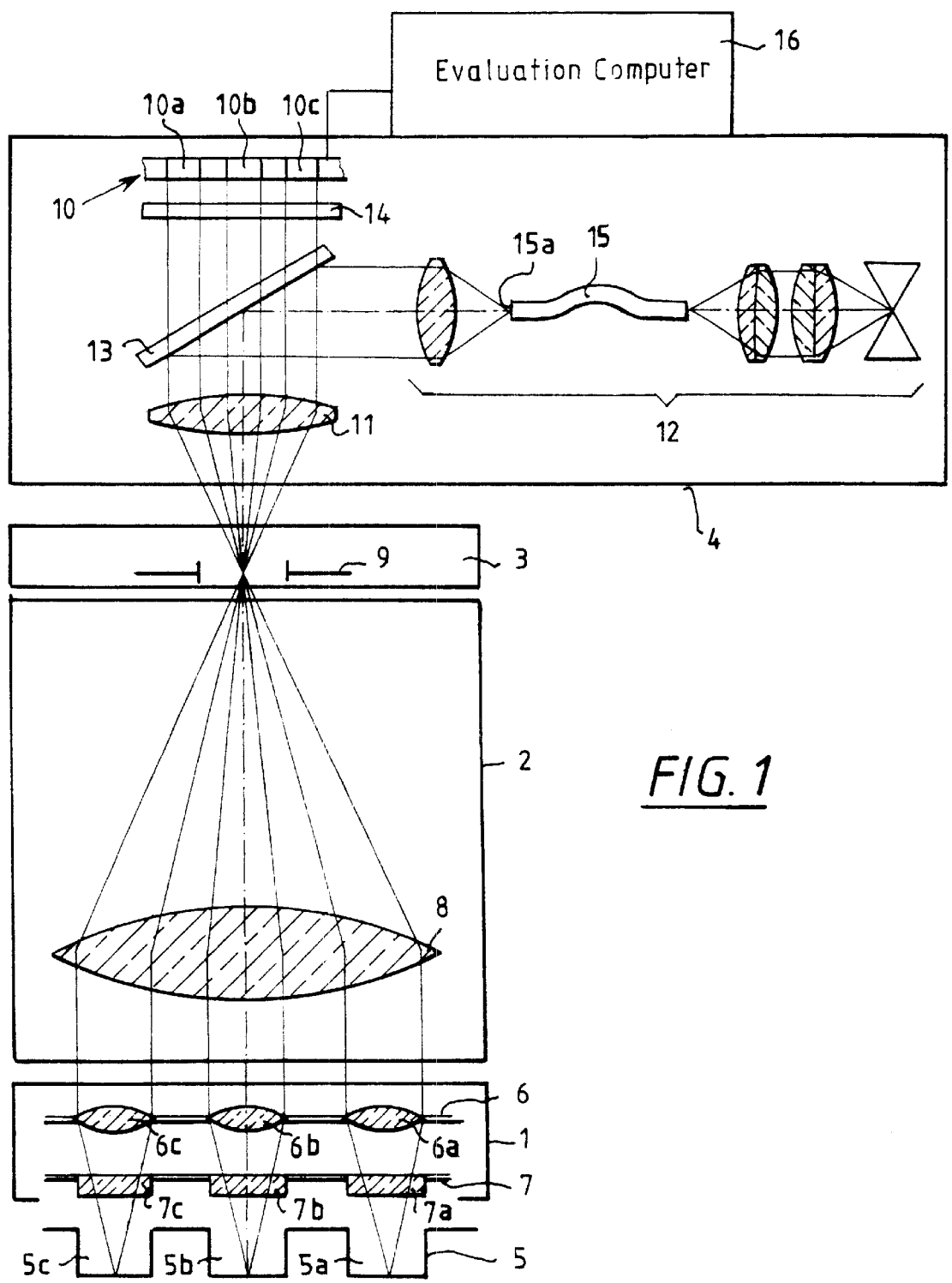
FIG. 1 shows an outline of principles of the optical construction of an analysis system with an imaging system according to the invention.

The measuring and evaluation system shown in FIG. 1 consists of a total of four modules (1–4), three of which contain optical components. It serves for the analysis, particularly fluorescence analysis, of the samples situated in sample containers (5a–5c) of a microtiter plate (5), as a rule cells lying on the floor of the sample containers (5a–5c) and surrounded by a nutrient solution.

The module (1) next adjacent to the microtiter plate (5) contains a lens array (6) with plural cylindrical lenses (6a–6c) and a prism array (7) with prisms (7a–7c). The prism array (7) is arranged on the sample side of the lens array (6), so that the prisms (7a–7c) are situated between the cylindrical lenses (6a–6c) and the sample containers (5a–5c). The prism array (7) or the prisms (7a–7c) of the prism array are then oriented relative to the cylindrical lens array (6) such that the prismatic effect of the prisms is in the direction of the cylinder axes of the cylindrical lenses (6a–6c).

A module (2) which contains a long-focus telescope lens (8) adjoins the side of the module (1) remote from the microtiter plate (5). The opening diameter, or more precisely the usable aperture, of the long-focus telescope lens (8) is then chosen such that this aperture overlaps the surface of all the apertures of the cylindrical lenses (6a–6c) of the cylindrical lens array. It should be mentioned at this point that for the sake of clarity, in FIG. 1 and the other Figures, respectively only a small section of the microtiter plate (5) with three sample containers is shown. In reality, 96, or an integral multiple thereof, 384 or 1536, corresponding sample containers are present, and there is a corresponding number of optical channels, which is determined by the number of microlenses (6a–6c) and of prisms (7a–7c). Correspondingly, the aperture of the long-focus telescope lens (8) overlaps all the optical channels.

In the region of the focal plane of the long-focus telescope lens (8), an intermediate module (3) follows the module (2) containing the long-focus telescope lens, and primarily serves as a spacer; with the exception of a diaphragm (9), it contains no optics. The diaphragm (9) forms an aperture stop in the direction of the cylinder axes of the cylindrical lenses (6a–6c), which in FIG. 1 stand perpendicular to the plane of the drawing. In the direction perpendicular thereto, and thus in the plane of the drawing of FIG. 1, the diaphragm (9) forms a field stop. In this direction, the diaphragm (9) has the effect that measurement light, for example fluorescence light, from the lateral edges of the sample holder (5a–5c) is screened off by the diaphragm (9) from the detector array (10).

Finally, the illumination and detector module (4) follows the intermediate module (3). It contains a short-focus telescope lens (11) which together with the long-focus telescope lens (8) forms an afocal system; the detector array (10); the vertical illuminator (12); and also an incident light reflector (13) arranged between the short-focus telescope lens (11) and the detector array (10). A fluorescence filter (14) with high transmission in the wavelength region of the fluorescence light or luminescence light and low transmission in the wavelength region of the excitation light of the vertical illuminator (12) is also arranged between the incident light reflector (13) and the detector array (10). Alternatively to this, the incident light reflector can also be constituted as a corresponding dichroic beamsplitter.

The vertical illuminator (12) produces a collimated illuminating beam path, the diameter of which corresponds to the aperture of the short-focus telescope lens (11). This illuminating pencil of rays is expanded to the aperture of the long-focus telescope lens (8) by the telescope formed by the lenses (8 and 11), and correspondingly illuminates all the apertures of the cylindrical lenses (6a) of the cylindrical lens array (6). A focusing of the excitation light by the cylindrical lenses (6a–6c) thus takes place in the direction perpendicular to the cylinder axes of the cylindrical lenses (6a–6c), and thus in the plane of the drawing of FIG. 1. In the direction perpendicular to this, on the other hand, the excitation light remains collimated, a deflection taking place due to the prismatic effect of the prisms (7a–7c), so that a number of line foci arise near the floors of the sample containers (5a–5c), and are inclined to the floors of the sample containers (5a–5c). The width of the line foci is then determined by the lateral dimensions of the effectively active light source, the exit surface (15a) of an optical fiber (15) in the vertical illuminator (12). The dimensions of this effectively active light source are then chosen so that a sufficiently large focal volume, and thus excitation volume, arises in the sample containers (5a–5c).

Figure 2B:
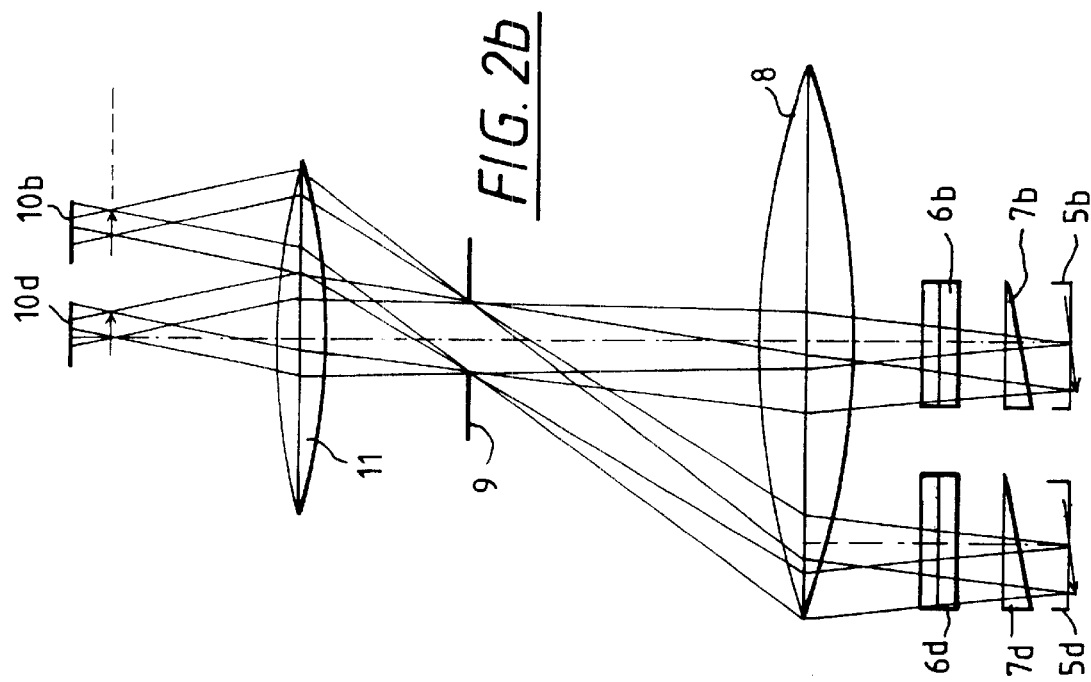
FIGS. 2a show the beam paths in the analysis system of FIG. 1, in and 2b two mutually perpendicular sectional directions.
Figure 2A:
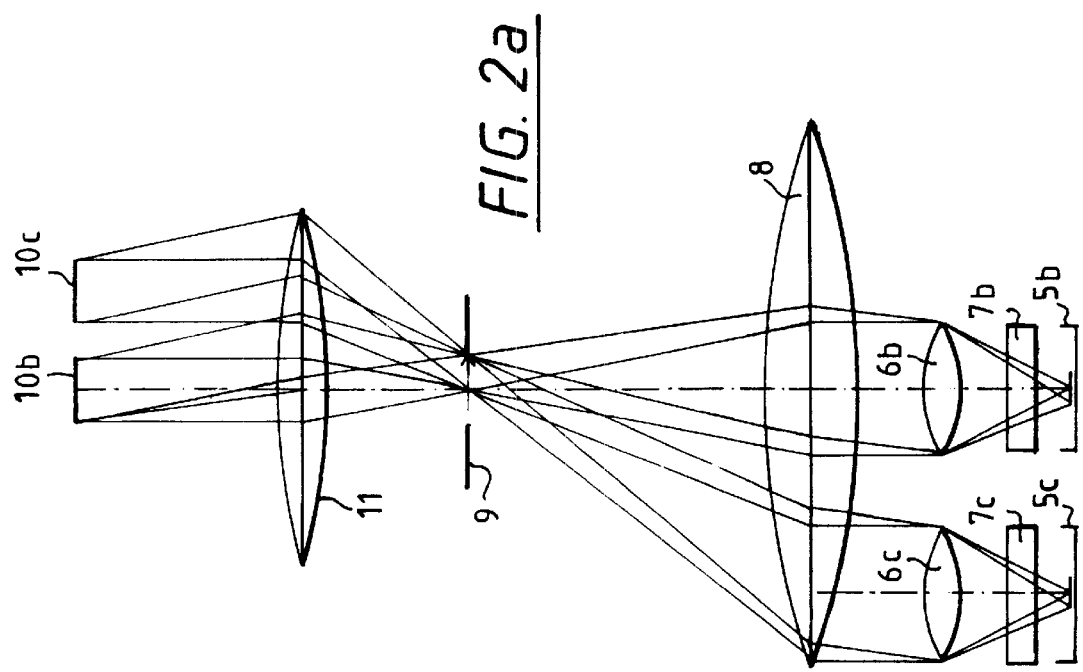

The transmission relationships on the imaging side are shown in FIGS. 2a and 2b for the two mutually perpendicular directions. The plane of the drawing in FIG. 2a then corresponds to the plane of the drawing in FIG. 1. The prism array (7) plays no part in the imaging relationships in this direction, since the prismatic effect of the prisms (7b, 7c) lies in the direction perpendicular to this. Since the cylindrical lenses (6b, 6c) have their effect in this direction, fluorescence radiation arising in the sample containers (5b, 5c) in the focal volume of the cylindrical lenses (6b, 6c) is collected with high aperture by the cylindrical lenses (6b, 6c) and is imaged by the long-focus telescope lens (8) in the focal plane of this long-focus telescope lens (8), and thus in the plane of the diaphragm (9). Superposed astigmatic intermediate images arise here, and are then imaged to infinity by the short-focus telescope lens (11). The fluorescence light is then detected by separate regions (10b, 10c) of the detector array (10). The pupils of the cylindrical lenses (6b, 6c) are thus imaged in the plane of the detector array, on separate regions of the detector array (10b, 10c), by the telescope formed by the two lenses (8,11).

In the direction of the cylinder axes of the cylindrical lenses (6b) (FIG. 2b), on the contrary, the cylindrical lenses have no effect. In this direction, the prisms (7b, 7d) of the prism array (7) of course have a prismatic effect. In this direction, the long-focus telescope lens (8) acts as the objective which collects the fluorescence light with relatively small aperture from the sample containers (5b, 5d). A deflection additionally takes place due to the prismatic effect of the prisms (7b, 7d), so that in this direction the foci of the individual channels are inclined to the focal plane of the long-focus telescope lens (8) and are thus inclined to the floors of the sample containers (5b, 5d). The sample containers (5b, 5d), and thus the microtiter plate, are arranged with the floors of the sample containers in the focal plane of the long-focus telescope lens (8). The fluorescence light collected by the long-focus telescope lens (8) is collimated by this, so that in this direction the diaphragm (9) acts as an aperture stop. Intermediate images of the foci of the long-focus telescope lens (8) arise in the rear focal plane (F2) of the short-focus telescope lens (11). The detector array with the regions (10b, 10d) is arranged slightly behind this focal plane.

Figure 3A:
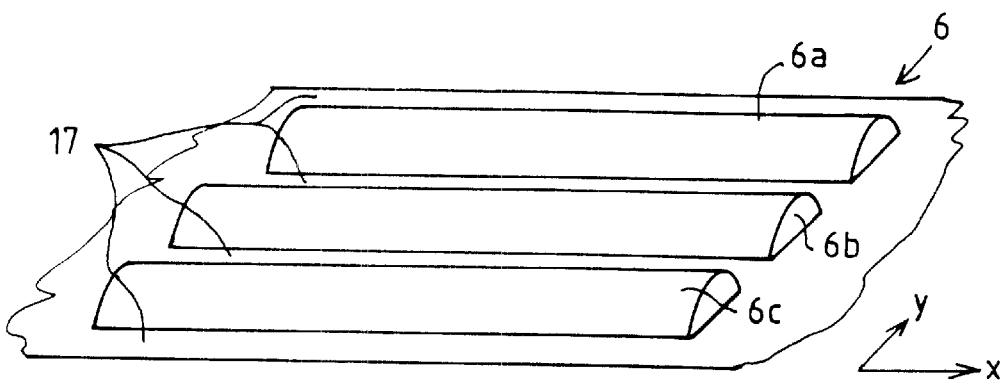
FIGS. 3a and 3b show details from perspective illustrations of the cylindrical lens array (FIG. 3a) and of the prism array (FIG. 3b).

The structure of the cylindrical lens array (6) is shown in FIG. 3a as a detail of the cylindrical lens array (6). The cylindrical lens array contains plural cylindrical lenses (6a, 6b, 6c), arranged mutually parallel and respectively able to extend over the whole length of the array in the direction of the cylinder axes. The regions (17) between the cylindrical lenses are preferably made opaque, for channel separation. A corresponding detail of the prism array (7) is shown in perspective in FIG. 3b. It contains a strip-shaped arrangement of prisms (7a, 7b, 7c), with respective prismatic effect in the direction of the cylinder axes of the cylindrical lenses (6a, 6b, 6c). In other words, each prism (7a, 7b, 7c) has an increasing or decreasing thickness in the direction of the cylinder axes. The prisms (7a, 7b, 7c) can extend over the whole length of the prism array (7) in the direction perpendicular to the cylinder axes of the cylindrical lenses (6a, 6b, 6c). The regions (18) between the prisms (7a, 7b, 7c) are again made opaque, for channel separation.

A two-dimensional array of optical channels, the number of which corresponds to the product of the number of cylindrical lenses and the number of prisms, arises by the superposition of the telescope lens array (6) and the prism array (7), and the opaque constitution of the interspaces (17, 18) between the cylindrical lenses or between the prisms.

Figure 3B:
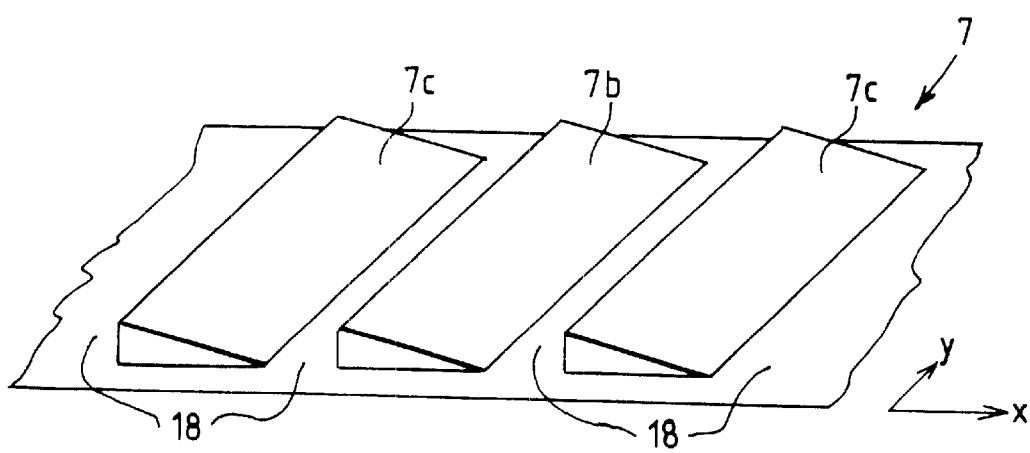

Alternatively to the constitution according to FIGS. 3a and 3b, it is however also conceivable to provide, for each optical channel, its own prism on the prism array and its own cylindrical lens on the cylindrical lens array. In this case, both the cylindrical lens array and the prism array are constituted as a two-dimensional array. A slightly better channel separation results from a corresponding opaque constitution of the interspaces; that is, crosstalk between the optical channels is reduced.

Figure 3C:
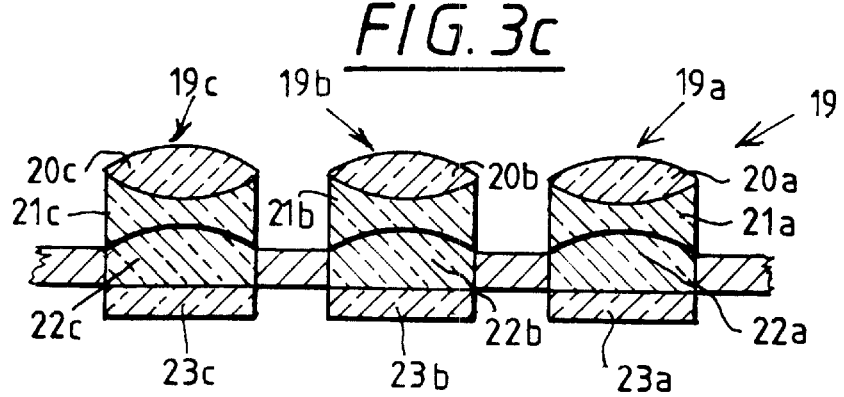
FIG. 3c shows a detail from an array with combined cylindrical lenses and prisms, in section.

A section through a combined cylindrical lens and prism array (19), which is achromatic over an extended spectral region, is shown in FIG. 3c. It contains, on a common support, a cylindrical lens and prism combination (19a, 19b, 19c) for each optical channel respectively consisting of three lenses (20a–20c, 21a–21c, 22a–22c) and prisms (23a–23c) following the lenses. In a manner known per se, the individual components of each cylindrical lens system consist of different materials, by means of which an achromatic correction is attained for a wavelength region of 350 nm–700 nm. The prisms (23a, 23b, 23c) again have a different thickness, from which the prismatic effect results, perpendicular to the plane of the drawing in FIG. 3, and thus in the direction of the cylinder axes of the cylindrical lenses.

The effect produced by the above-described arrangement in the region of the sample space floor can be seen from FIGS. 4a and 4b. The sample space floors (24a, 24b) are shown there for two exemplary adjacent cells of the microtiter plate. It is to be assumed here that the two sample space floors are mutually displaced by a small distance (h). The focal volumes of the relevant optical channels in the two sample spaces are denoted by (25a, 25b). These focus volumes are circular cylinders, the cylinder axis being respectively inclined to the plane of the sample space floor. The inclination between the plane of the sample space floor and the cylinder axes of the focus volumes (25a, 25b) is then determined by the prismatic effect of the prisms. The diameter of the cylindrical focus volumes is substantially determined by the numerical aperture of the whole arrangement, primarily the numerical aperture of the cylindrical lenses being considerable here. Numerical apertures in this direction of 0.5 or more can be attained without problems.

As can be recognized from a comparison of FIGS. 4a and 4b, a lateral displacement of the relevant sectional plane between the cylindrical focus volume and the surface of the sample space floor results from different floor heights in the different cells of the microtiter plate, because of the inclination of the focus volumes to the plane of the sample space floor. The different intensity distributions of the fluorescence radiation thereby arising in the regions (10a–10c) on the detector array are correspondingly shown in FIGS. 5a and 5b. By a displacement of the sectional plane between the focus volume and the sample space floor, there results a corresponding displacement of the intensity distribution in the direction of the cylinder axes of the cylindrical lens array, since the fluorescence intensity is as a rule maximum in the immediate neighborhood of the sample space floor. For signal evaluation, in an evaluation computer (16), the intensity signals of the pixels of the detector array belonging to each sample space or each optical channel are first integrated in a direction perpendicular to the cylinder axes of the cylindrical lenses, and subsequently the characteristic signal change in the direction of the cylinder axes, as a rule the maximum, of the integrated fluorescence intensity is determined and evaluated. In measurements of reaction kinetics or of the time course of the fluorescence signal, the fluorescence measurement takes place repeatedly over plural receiving and readout cycles of the detector array.

It has been found to be appropriate to dimension the prisms of the prism array such that the cylindrical focus volumes (25a, 25b) cover a region of 0.3–0.5 mm in the direction of the optical axis of the whole arrangement. The length of the cylindrical focus volume preferably extends over the whole corresponding length of the sample space, which corresponds to about 3 mm for a 384-well microtiter plate. A substantially elliptical intersection surface between the sample space floor and the focus volume then results due to the inclination of the cylindrical focus volume, and has a major axis of about 1 mm and a minor axis of about 0.13 mm.

FIG. 6a shows an interchange module or supplementary module (31) for interchange with a module (1) in the arrangement according to FIG. 1. The interchange module (31) contains a lens array with rotationally symmetrical lenses (32a–32c). A further interchange module (33) (FIG. 6b) for interchange with the module (3) contains a field lens (34). Interchange of the modules (31) and (33) with the modules (1) and (3) in FIG. 1 results in an optical arrangement which corresponds to the optics according to the above-cited patent application 197 48 211. Compatibility with the optical arrangement described in the older application is thus ensured by corresponding additional modules.

What is claimed is:

1. Imaging system with an array (6) of cylindrical lenses (6a, 6b, 6c) and with a prism array (7) combined with, or arranged before, the array of cylindrical lenses, wherein the prismatic effect of the prisms (7a, 7b, 7c) is in the direction of the cylinder axes of the cylindrical lenses (6a, 6b, 6c), so that the cylinder axes of the substantially cylindrical focal volumes of the cylindrical lenses receive an inclination relative to the cylinder axes of the cylindrical lenses.

2. Imaging system according to claim 1, wherein a detector array (10) and a telescopic imaging system are provided, wherein the telescope imaging system is arranged between the array (6) of cylindrical lenses (6a, 6b, 6c) and the detector array (10) and wherein the prism array (7) is arranged on the side of the array (6) of cylindrical lenses (6a, 6b, 6c) remote from the telescopic image system.

3. Imaging system according to claim 2, wherein the long-focus lens (8) of the telescopic imaging system is arranged adjoining the array (6) of cylindrical lenses (6a, 6b, 6c), and its diameter overlaps several cylindrical lenses (6a, 6b, 6c).

4. Imaging system according to claim 2, wherein the detector array (10) is arranged behind the exit-side focal plane (F2) of the telescope lens (11) remote from the cylindrical lens array (6).

5. Imaging system according to claim 2, wherein the apertures of the cylindrical lenses (6a, 6b, 6c) are imaged on the detector array (10) by means of the telescopic imaging system (8, 11).

6. Imaging system according to claim 1, wherein the cylindrical lens array (6) and/or the prism array (7) are strip-shaped.

7. Imaging system according to claim 2, wherein a vertical illuminator (12) is provided which is reflected between the detector array (10) and the short-focus lens of the telescopic imaging system into the beam path leading into the array (6) of cylindrical lenses (6a, 6b, 6c).

8. Automatic analyzer with an optical imaging system according to claim 2, wherein an evaluation of the optical signals detected with the detector array (10).

9. Imaging system of modular construction, consisting of:

a first constructional unit (1) with an array of cylindrical lenses and a prism array combined with, or arranged before, the array of cylindrical lenses, wherein the prismatic effect of the prisms (7a, 7b, 7c) is in the direction of the cylinder axes of the cylindrical lenses (6a, 6b, 6c), a second constructional unit with a long-focus optics (8), the free usable aperture diameter of which overlaps the diameter of the cylindrical lens array (6), a third constructional unit (4) with a short-focus optics (11), which in common with the long-focus optics (8) of the second constructional unit forma an afocal system, and a fourth constructional unit (3) without imaging optics, arranged between the second constructional unit (2) and the third constructional unit (4).

10. Imaging system of modular construction according to claim 9, wherein two further constructional units (31, 33) are provided, of which the one is an array (32) with rotationally symmetrical individual lenses (32a–32c) for interchange with the first constructional unit (1), and the second additional constructional unit (33) has a field lens (34) and is interchangeable with the fourth constructional unit.

* * * * *